United States Patent [19]
Aviv et al.

[11] Patent Number: 5,970,978
[45] Date of Patent: Oct. 26, 1999

[54] MEASUREMENTS OF RESPIRATORY SENSORY DISCRIMINATION THRESHOLDS

[75] Inventors: Jonathan E. Aviv, New York; John H. Martin, Valley Cottage, both of N.Y.

[73] Assignee: The Trustees of Columbia University, New York, N.Y.

[21] Appl. No.: 08/817,197

[22] PCT Filed: Oct. 13, 1995

[86] PCT No.: PCT/US95/13039

§ 371 Date: Jun. 12, 1997

§ 102(e) Date: Jun. 12, 1997

[87] PCT Pub. No.: WO96/11627

PCT Pub. Date: Apr. 25, 1996

Related U.S. Application Data

[63] Continuation-in-part of application No. 08/323,499, Oct. 14, 1994, Pat. No. 5,515,860.

[51] Int. Cl.[6] .................................................. A61M 16/00
[52] U.S. Cl. .............................. 128/207.14; 128/203.12; 600/587
[58] Field of Search ......................... 128/207.14, 203.12, 128/204.18, 204.23, 204.21, 200.24; 600/560, 587, 593

[56] References Cited

U.S. PATENT DOCUMENTS 5,515,860   5/1996   Aviv et al. .............................. 128/745

*Primary Examiner*—John G. Weiss
*Assistant Examiner*—Charles W. Anderson
*Attorney, Agent, or Firm*—John P. White; Cooper & Dunham LLP

[57] ABSTRACT

An apparatus and method to objectively measure sensory discrimination thresholds at a test site in the upper aero digestive tract of a patient. A time and pressure controlled puff of air is delivered to the input of a Y-shaped tube; one output branch of the Y-shaped tube delivers the puff of air to the patient and the other output branch delivers the puff of air to a pressure transducer, for measurement and display of the pressure.

21 Claims, 6 Drawing Sheets

5,970,978

MEASUREMENTS OF RESPIRATORY SENSORY DISCRIMINATION THRESHOLDS

This is a continuation-in-part of application Ser. No. 08/323,499, filed Oct. 14, 1994 now Pat. No. 5,515,860.

BACKGROUND OF THE INVENTION

The present invention relates to an apparatus and a method to objectively measure sensory discrimination thresholds by delivering a time and pressure controlled air puff to the upper aero digestive tract, including, for example, the oral cavity, pharynx, or supraglottic larynx of a patient.

Within this application several publications are referenced by Arabic numerals within parentheses. Full citations for these and other references may be found at the end of the specification immediately preceding the claims. The disclosures of all of these publications in their entireties are hereby incorporated by reference into this application in order to more fully describe the state of the art to which this invention pertains.

There is a dearth of published studies of supraglottic and pharyngeal sensation in normal healthy controls, in the elderly, or in those who have suffered from a cerebrovascular accident (CVA). One of the primary problems with measuring sensation in this region (the area innervated by the superior laryngeal nerve) is the presence of the gag reflex and the relative inaccessibility of this area in awake individuals. These obstacles preclude standard sensory discrimination tests such as static and moving two point discrimination, vibratory testing, and stereognosis (1).

Knowledge of pharyngeal and supraglottic sensory discrimination thresholds is particularly important since hypesthesia or anesthesia in this area of the head and neck can cause severe dysphagia and an increased frequency of aspiration. Dysphagia and aspiration are commonly seen in the elderly (2), in those who have suffered a stroke (3), and in patients who have had ablative cancer surgery of the pharynx and larynx (4, 5) and/or loss of cranial nerves. The development of treatment modalities which address the sensory deficits in the pharynx and larynx is dependent upon defining and quantifying the sensory deficits in this region. The first step towards this goal is to establish normal thresholds for sensory discrimination.

However, as of yet, it appears that no one has been able to achieve this first step of measuring pharyngeal sensation in healthy control subjects, much less than in stroke patients with dysphagia. In other medical fields, air pulse stimulation of the cornea, or pneumatic tonometry has been used by ophthalmologists in order to measure intraocular pressure (6). Sensory discrimination testing using this technique, however, was not applied to the cornea. Air pulse stimuli have also been used as a natural stimulus to study the mechanisms whereby somatosensory systems analyze sensory stimulus patterns (7, 8). Furthermore air pulse stimuli have been shown to be an extremely sensitive and reliable method of determining sensory discrimination thresholds in the upper extremity of man (8, 9). However, it appears that no previous method of sensory testing of the upper aero digestive tract, including specifically the oral cavity, supraglottic larynx, or pharynx has been described.

SUMMARY OF THE INVENTION

It is an object of the present invention to provide an arrangement for testing and determining the sensory discrimination threshold in an individual at a test site in the upper aero digestive tract.

It is a further object of the present invention to provide an arrangement for testing and determining the supraglottic and pharyngeal sensory discrimination threshold in an individual.

It is a further object of the present invention to provide an arrangement for testing and determining the supraglottic and pharyngeal sensory discrimination threshold in an individual without causing excessive gagging.

It is a yet further object of the present invention to provide an arrangement for testing and determining the supraglottic and pharyngeal sensory discrimination threshold in an individual during an otherwise standard laryngoscopic examination.

According to one aspect of the present invention, an apparatus for testing sensation in a patient at a test site in the upper aero digestive tract is provided, comprising means for generating a time and pressure controlled puff of air and means, connected to said means for generating, for delivering the controlled puff of air to the test site.

According to another aspect of the present invention, an apparatus for testing pharyngeal and supraglottic sensation in a patient at a test site in the pharynx or larynx region is provided, comprising means for generating a time and pressure controlled puff of air and means, connected to said means for generating, for delivering the controlled puff of air to the pharynx or larynx region.

According to another aspect of the invention, an apparatus for testing sensation in a patient at a test site in the upper aero digestive tract is provided, comprising a Y-shaped tube with an inlet branch having an inlet end and first and second outlet branches having respective first and second outlet ends, the first outlet branch of the Y-shaped tube being inserted into the patient's nasal passage and the first outlet end terminating adjacent the test site. A pressure transducer is connected to the second outlet branch of the Y-shaped tube, axially aligned with the second outlet end, means for delivering a time and pressure controlled puff of air to the inlet end of the Y-shaped tube is provided, as well as display means responsive to the pressure transducer for displaying the value of pressure detected by the transducer.

According to another aspect of the present invention, an apparatus for testing sensation in a patient at a test site in the upper aero digestive tract is provided, comprising a Y-connector with an inlet end and first and second outlet ends, a pressure transducer, means for delivering a time and pressure controlled puff of air to the inlet end of the Y-connector, a delivery tube with an inlet end and an outlet end, the delivery tube inlet end being connected to the first outlet end of the Y-connector and the delivery tube outlet end being inserted into the patient's nasal passage and terminating adjacent the test site, a sensor tube with an inlet end and an outlet end, the sensor tube inlet end being connected to the second outlet end of the Y-connector and the sensor tube outlet end being connected to the pressure transducer, and display means responsive to the pressure transducer for displaying the value of pressure detected by the transducer.

According to another aspect of the present invention, an apparatus for testing sensation in a patient at a test site in the upper aero digestive tract is provided, comprising a flexible fiberoptic telescope inserted at its distal end into the patient's nasal passage, the distal end terminating adjacent the test site, a Y-connector with an inlet end and first and second outlet ends, a delivery tube with an inlet end and an outlet end, the delivery tube being attached to the fiberoptic telescope with the outlet end of the delivery tube adjacent the distal end of the fiberoptic telescope and the inlet end of the delivery tube extending outside the patient and being attached to the first outlet end of the Y-connector, a pressure transducer, a sensor tube with an inlet end and an outlet end, the sensor tube inlet end being connected to the second outlet end of the Y-connector and the sensor tube outlet end being connected to the pressure transducer, means for delivering a time and pressure controlled puff of air to the inlet end of the Y-connector, and display means responsive to the pressure transducer for displaying the value of pressure detected by the transducer.

According to another aspect of the present invention, a method for testing sensation in a patient at a test site in the upper aero digestive tract is provided, comprising generating a time and pressure controlled puff of air and delivering the controlled puff of air to the test site.

According to another aspect of the present invention, a method for testing pharyngeal and supraglottic sensation in a patient at a test site in the pharynx or larynx region is provided, comprising generating a time and pressure controlled puff of air and delivering the controlled puff of air to the pharynx or larynx region.

According to another aspect of the present invention, a method for testing pharyngeal and supraglottic sensation in a patient at a test site in the pharynx or larynx region is provided, comprising generating six blocks of time and pressure controlled puffs of air, each block including ten puffs of air, each succeeding puff of air in a block differing by a pressure of about $7.5 \times 10^{-2}$ mm Hg as compared to the preceding puff of air, and delivering each block of time and pressure controlled puffs of air to the pharynx or larynx region, with a rest period between blocks of about 30 seconds.

According to another aspect of the present invention, a method for testing pharyngeal and supraglottic sensation in a patient at a test site in the pharynx or larynx region is provided, comprising inserting a first outlet end of a Y-shaped tube into the patent's nasal passage adjacent the test site, delivering a time and pressure controlled puff of air to an inlet end of the Y-shaped tube, measuring the air pressure at a second outlet end of the Y-shaped tube, and displaying the measured air pressure.

According to another aspect of the invention, an apparatus for testing sensation in a patient at a test site in the upper aero digestive tract is provided, comprising a flexible fiberoptic telescope with an input port at a first end and an output port at a second end, said input port being in communication with said output port, said flexible fiberoptic telescope being adapted to be inserted at its second end into one of the patient's nasal passage and oral passage, the second end terminating adjacent the test site, a Y-connector with an inlet end and first and second outlet ends, a delivery tube with an inlet end and an outlet end, the outlet end of the delivery tube being attached to the input port of the flexible fiberoptic telescope and the inlet end of the delivery tube being attached to the first outlet end of the Y-connector, a pressure transducer, a sensor tube with an inlet end and an outlet end, the sensor tube inlet end being connected to the second outlet end of the Y-connector and the sensor tube outlet end being connected to the pressure transducer, means for delivering a time and pressure controlled puff of air to the inlet end of the Y-connector, and display means responsive to the pressure transducer for displaying a value of pressure detected by the transducer.

According to another aspect of the invention, a method for testing sensation in a patient at a test site in the upper aero digestive tract is provided, comprising connecting a first outlet end of a Y-shaped tube to an input end of an insertion tube section of a flexible fiberoptic telescope, inserting the insertion tube section of the flexible fiberoptic telescope into one of the patient's nasal passage and oral passage so that an output end of the insertion tube section is adjacent the test site, delivering a time and pressure controlled puff of air to an inlet end of the Y-shaped tube, measuring the air pressure at a second outlet end of the Y-shaped tube, and displaying the measured air pressure.

According to another aspect of the present invention an apparatus for testing sensation in a patient at a test site is provided, comprising control means for setting a time duration value and a pressure value of a time and pressure controlled puff of air, means for generating the time and pressure controlled puff of air in response to said set time duration value and said set pressure value, and means, connected to said means for generating, for delivering the controlled puff of air to the test site.

According to another aspect of the instant invention an apparatus for testing sensation in a patient at a test site is provided, comprising a Y-shaped tube with an inlet branch having an inlet end and first and second outlet branches having respective first and second outlet ends, the first outlet branch of the Y-shaped tube being inserted into one of the patient's nasal passage and oral passage, the first outlet end terminating adjacent the test site, a pressure transducer connected to the second outlet branch of the Y-shaped tube, axially aligned with the second outlet end, means for delivering a time and pressure controlled puff of air detachably connected to the inlet end of the Y-shaped tube, and display means responsive to the pressure transducer for displaying a value of pressure detected by the transducer.

According to another aspect of the instant invention an apparatus for testing sensation in a patient at a test site is provided, comprising a Y-connector with an inlet end and first and second outlet ends, a pressure transducer, means for delivering a time and pressure controlled puff of air to the inlet end of the Y-connector, a delivery tube with an inlet end and an outlet end, the delivery tube inlet end being connected to the first outlet end of the Y-connector and the delivery tube outlet end being inserted into the patient's nasal passage and terminating adjacent the test site, a sensor tube with an inlet end and an outlet end, the sensor tube inlet end being connected to the second outlet end of the Y-connector and the sensor tube outlet end being connected to the pressure transducer, and display means responsive to the pressure transducer for displaying a value of pressure detected by the transducer.

According to another aspect of the instant invention an apparatus for testing sensation in a patient at a test site is provided, comprising a flexible fiberoptic telescope inserted at its distal end into one of the patient's nasal passage and oral passage, the distal end terminating adjacent the test site, a Y-connector with an inlet end and first and second outlet ends, a delivery tube with an inlet end and an outlet end, the delivery tube being detachably attached to the fiberoptic telescope with the outlet end of the delivery tube adjacent the distal end of the fiberoptic telescope and the inlet end of the delivery tube extending outside the patient and being detachably attached to the first outlet end of the Y-connector, a pressure transducer, a sensor tube with an inlet end and an outlet end, the sensor tube inlet end being connected to the second outlet end of the Y-connector and the sensor tube outlet end being connected to the pressure transducer, means for delivering a time and pressure controlled puff of air to the inlet end of the Y-connector, and display means responsive to the pressure transducer for displaying a value of pressure detected by the transducer.

According to another aspect of the instant invention a method for testing sensation in a patient at a test site is provided, comprising generating a time and pressure controlled puff of air, and delivering the controlled puff of air to the test site.

According to another aspect of the instant invention a method for testing sensation in a patient at a test site is provided, comprising generating six blocks of time and pressure controlled puffs of air, each block including ten puffs of air, each succeeding puff of air in a block differing by a pressure of about $7.5 \times 10^{-2}$ mm Hg as compared to the preceding puff of air, and delivering each block of time and pressure controlled puffs of air to the test site, with a rest period between blocks of about 30 seconds.

According to another aspect of the instant invention a method for testing sensation in a patient at a test site is provided, comprising inserting a first outlet end of a Y-shaped tube into one of the patent's nasal passage and oral passage adjacent the test site, delivering a time and pressure controlled puff of air to an inlet end of the Y-shaped tube, measuring the air pressure at a second outlet end of the Y-shaped tube, and displaying the measured air pressure.

According to another aspect of the instant invention an apparatus for testing sensation in a patient at a test site is provided, comprising a flexible fiberoptic telescope with an input port at a first end and an output port at a second end, said input port being in communication with said output port, said flexible fiberoptic telescope being adapted to be inserted at its second end into one of the patient's nasal passage and oral passage, the second end terminating adjacent the test site, a Y-connector with an inlet end and first and second outlet ends, a delivery tube with an inlet end and an outlet end, the outlet end of the delivery tube being attached to the input port of the flexible fiberoptic telescope and the inlet end of the delivery tube being attached to the first outlet end of the Y-connector, a pressure transducer, a sensor tube with an inlet end and an outlet end, the sensor tube inlet end being connected to the second outlet end of the Y-connector and the sensor tube outlet end being connected to the pressure transducer, means for delivering a time and pressure controlled puff of air to the inlet end of the Y-connector, and display means responsive to the pressure transducer for displaying a value of pressure detected by the transducer.

According to another aspect of the instant invention a method for testing sensation in a patient at a test site is provided, comprising connecting a first outlet end of a Y-shaped tube to an input end of an insertion tube section of a flexible fiberoptic telescope, inserting the insertion tube section of the flexible fiberoptic telescope into one of the patient's nasal passage and oral passage so that an output end of the insertion tube section is adjacent the test site, delivering a time and pressure controlled puff of air to an inlet end of the Y-shaped tube, measuring the air pressure at a second outlet end of the Y-shaped tube, and displaying the measured air pressure.

According to another aspect of the instant invention a method for testing sensation in a patient at a test site is provided, comprising generating a time and pressure controlled puff of air, delivering the controlled puff of air to the test site, and observing when an involuntary reflex occurs in the area of the test site.

According to another aspect of the instant invention a method for testing sensation in a patient at a test site is provided, comprising generating six blocks of time and pressure controlled puffs of air, each block including ten puffs of air, each succeeding puff of air in a block differing by a pressure of about 0.2 mm Hg as compared to the preceding puff of air, delivering each block of time and pressure controlled puffs of air to the test site, with a rest period between blocks of about 30 seconds, and observing when an involuntary reflex occurs in the area of the test site.

These and other advantages will become apparent from the detailed description accompanying the claims and attached drawing figures.

DETAILED DESCRIPTION OF THE PREFERRED EMBODIMENTS

Figure 1:
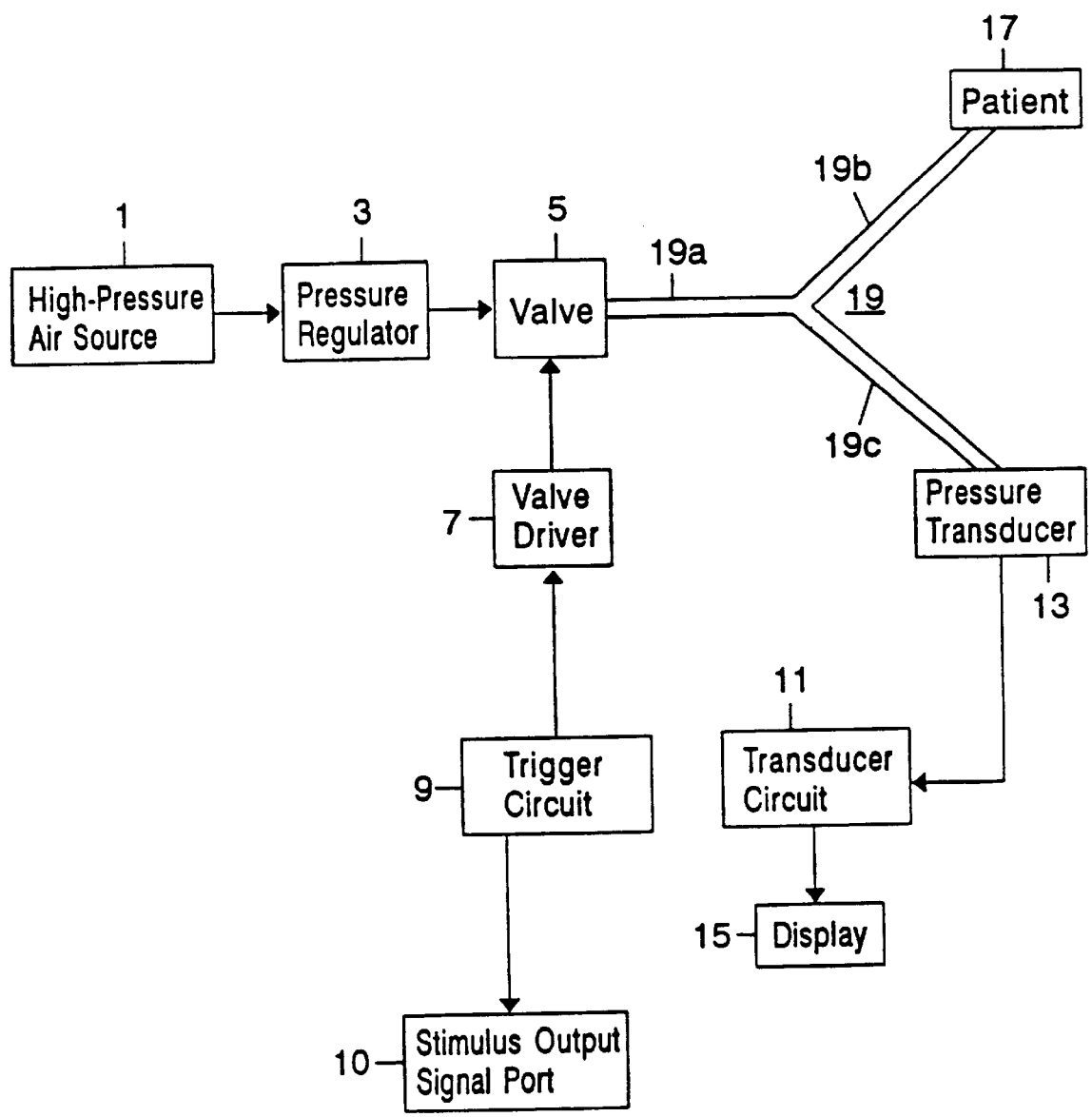
FIG. 1 is an upper aero digestive tract sensation measurement apparatus according to a first embodiment of the present invention.

According to one aspect of the present invention, an apparatus for testing sensation in a patient at a test site in the upper aero digestive tract is provided, comprising means for generating a time and pressure controlled puff of air and means, connected to said means for generating, for delivering the controlled puff of air to the test site.

The means for generating a time and pressure controlled puff of air preferably comprises a source of high pressure air, a pressure regulator receiving the high pressure air, a valve receiving regulated air from the pressure regulator, and means for controllably driving the valve to open and closed positions.

The means for controllably driving the valve to open and closed positions preferably comprises a trigger circuit producing trigger signals, a valve driver producing drive signals responsive to the trigger signals input from the trigger circuit, and an electrically controlled valve, the open or closed state of which is responsive to drive signals input from the valve driver. The trigger circuit may produce variable duration trigger signals.

The apparatus may include a means responsive to the trigger signals of the trigger circuit for outputting stimulus output signals which mark the stimulus output, that is, the time and pressure controlled puff of air. The stimulus output signal, which may be a TTL signal, may serve as a trigger for an oscilloscope and/or for physiological recordings. These recordings may include EMG (electromyography) changes in oral cavity, laryngeal, pharyngeal, and esophageal musculature. The stimulus output signal may also be used for synchronizing computer averaging for recording of sensory evoked potentials such as cortical, sub-cortical, and brain-stem evoked responses, as well as other electroencephalographic changes. Such recordings enable non-invasive analysis of both the peripheral nervous system and the brain in conscious and unconscious patients.

According to another aspect of the present invention, an apparatus for testing pharyngeal and supraglottic sensation in a patient at a test site in the pharynx or larynx region is provided, comprising means for generating a time and pressure controlled puff of air and means, connected to said means for generating, for delivering the controlled puff of air to the pharynx or larynx region.

The means for generating a time and pressure controlled puff of air preferably comprises a source of high pressure air, a pressure regulator receiving the high pressure air, a valve receiving regulated air from the pressure regulator, and means for controllably driving the valve to open and closed positions.

The means for controllably driving the valve to open and closed positions preferably comprises a trigger circuit producing trigger signals, a valve driver producing drive signals responsive to the trigger signals input from the trigger circuit, and an electrically controlled valve, the open or closed state of which is responsive to drive signals input from the valve driver. The trigger circuit may produce variable duration trigger signals.

The present invention also provides an apparatus for testing sensation in a patient at a test site in the upper aero digestive tract, comprising a Y-shaped tube with an inlet branch having an inlet end and first and second outlet branches having respective first and second outlet ends, the first outlet branch of the Y-shaped tube being inserted into the patient's nasal passage, the first outlet end terminating adjacent the test site, a pressure transducer connected to the second outlet branch of the Y-shaped tube, axially aligned with the second outlet end, means for delivering a time and pressure controlled puff of air to the inlet end of the Y-shaped tube, and display means responsive to the pressure transducer for displaying the value of pressure detected by the transducer. The first and second outlet branches may be substantially the same length.

The means for delivering a time and pressure controlled puff of air to the inlet end of the Y-shaped tube preferably comprises a source of high pressure air, a pressure regulator receiving the high pressure air, a valve, connected between the pressure regulator and the inlet end of the Y-shaped tube, receiving regulated air from the pressure regulator, and means for controllably driving the valve to open and closed positions.

The means for controllably driving the valve to open and closed positions preferably comprises a trigger circuit producing trigger signals, a valve driver producing drive signals responsive to the trigger signals input from the trigger circuit, and an electrically controlled valve, the open or closed state of which is responsive to drive signals input from the valve driver. The trigger circuit may produce variable duration trigger signals.

The display means responsive to the pressure transducer for displaying the value of pressure detected by the transducer preferably comprises a transducer circuit responsive to input from the pressure transducer and a display responsive to input from the transducer circuit. The display may be a Light Emitting Diode display.

The pressure transducer may be connected to the second outlet branch of the Y-shaped tube about 2 mm from the second outlet when the test site is about 2 mm from the anterior wall of the patient's pyriform sinus.

According to another aspect of the invention, an apparatus for testing sensation in a patient at a test site in the upper aero digestive tract is provided, comprising a Y-connector with an inlet end and first and second outlet ends, a pressure transducer, means for delivering a time and pressure controlled puff of air to the inlet end of the Y-connector, a delivery tube with an inlet end and an outlet end, the delivery tube inlet end being connected to the first outlet end of the Y-connector and the delivery tube outlet end being inserted into the patient's nasal passage and terminating adjacent the test site, a sensor tube with an inlet end and an outlet end, the sensor tube inlet end being connected to the second outlet end of the Y-connector and the sensor tube outlet end being connected to the pressure transducer, and display means responsive to the pressure transducer for displaying the value of pressure detected by the transducer. The delivery tube and the sensor tube may be substantially the same length.

According to another aspect of the invention, an apparatus for testing sensation in a patient at a test site in the upper aero digestive tract is provided, comprising a flexible fiberoptic telescope inserted at its distal end into the patient's nasal passage, the distal end terminating adjacent the test site, a Y-connector with an inlet end and first and second outlet ends, a delivery tube with an inlet end and an outlet end, the delivery tube being attached to the fiberoptic telescope with the outlet end of the delivery tube adjacent the distal end of the fiberoptic telescope and the inlet end of the delivery tube extending outside the patient and being attached to the first outlet end of the Y-connector, a pressure transducer, a sensor tube with an inlet end and an outlet end, the sensor tube inlet end being connected to the second outlet end of the Y-connector and the sensor tube outlet end being connected to the pressure transducer, means for delivering a time and pressure controlled puff of air to the inlet end of the Y-connector, and display means responsive to the pressure transducer for displaying the value of pressure detected by the transducer. The delivery tube and the sensor tube may be substantially the same length.

A method for testing sensation in a patient at a test site in the upper aero digestive tract is also provided in accordance with the invention, comprising generating a time and pressure controlled puff of air and delivering the controlled puff of air to the test site.

The method for testing sensation in a patient at a test site may include the steps of generating a plurality of time and pressure controlled puffs of air, each succeeding puff of air being of a higher pressure than the last, and delivering the plurality of time and pressure controlled puffs of air to the test site in sequence.

The step of generating a plurality of time and pressure controlled puffs of air may further include the step of generating, as a first puff, a puff of air with a subliminal pressure, and as a last puff, a puff of air with a supraliminal pressure. The difference between succeeding puffs of air may be about $7.5 \times 10^{-2}$ mm Hg.

The method may include the step of outputting a stimulus output signal when the controlled puff of air is delivered.

According to another aspect of the invention, the method for testing sensation in a patient at a test site in the upper aero digestive tract may include generating a plurality of time and pressure controlled puffs of air, each succeeding puff of air being of a lower pressure than the last, and delivering the plurality of time and pressure controlled puffs of air to test site in sequence.

The step of generating a plurality of time and pressure controlled puffs of air may include the step of generating, as a first puff, a puff of air with a supraliminal pressure, and as a last puff, a puff of air with a subliminal pressure. The difference between succeeding puffs of air may be about $7.5 \times 10^{-2}$ mm Hg.

A method for testing pharyngeal and supraglottic sensation in a patient at a test site in the pharynx or larynx region is also provided in accordance with the invention, comprising generating a time and pressure controlled puff of air and delivering the controlled puff of air to the pharynx or larynx region.

The method for testing pharyngeal and supraglottic sensation in a patient at a test site in the pharynx or larynx region may include the steps of generating a plurality of time and pressure controlled puffs of air, each succeeding puff of air being of a higher pressure than the last, and delivering the plurality of time and pressure controlled puffs of air to the pharynx or larynx region in sequence.

The step of generating a plurality of time and pressure controlled puffs of air may further include the step of generating, as a first puff, a puff of air with a subliminal pressure, and as a last puff, a puff of air with a supraliminal pressure. The difference between succeeding puffs of air may be about $7.5 \times 10^{-2}$ mm Hg.

According to another aspect of the invention, the method for testing pharyngeal and supraglottic sensation in a patient at a test site in the pharynx or larynx region may include generating a plurality of time and pressure controlled puffs of air, each succeeding puff of air being of a lower pressure than the last, and delivering the plurality of time and pressure controlled puffs of air to the pharynx or larynx region.

The step of generating a plurality of time and pressure controlled puffs of air may include the step of generating, as a first puff, a puff of air with a supraliminal pressure, and as a last puff, a puff of air with a subliminal pressure. The difference between succeeding puffs of air may be about $7.5 \times 10^{-2}$ mm Hg.

According to another aspect of the invention, a method for testing pharyngeal and supraglottic sensation in a patient at a test site in the pharynx or larynx region is provided, comprising generating six blocks of time and pressure controlled puffs of air, each block including ten puffs of air, each succeeding puff of air in a block differing by a pressure of about $7.5 \times 10^{-2}$ mm Hg as compared to the preceding puff of air, and delivering each block of time and pressure controlled puffs of air to the pharynx or larynx region, with a rest period between blocks of about 30 seconds.

The step of delivering each block of time and pressure controlled puffs of air to the pharynx or larynx region may include delivering each puff of air at a random time within a ten second window. The pressure of the first puff of air in about one-half of the blocks may be subliminal and the last puff of air may be supraliminal, and the pressure of the first puff of air in the other one-half of the blocks may be supraliminal and the pressure of the last puff of air may be subliminal.

According to another aspect of the invention, a method for testing pharyngeal and supraglottic sensation in a patient at a test site in the pharynx or larynx region is provided, comprising inserting a first outlet end of a Y-shaped tube into the patent's nasal passage adjacent the test site, delivering a time and pressure controlled puff of air to an inlet end of the Y-shaped tube, measuring the air pressure at a second outlet end of the Y-shaped tube, and displaying the measured air pressure.

The step of inserting the first outlet end of the Y-shaped tube into a patent's nasal passage adjacent the test site may include inserting the first outlet end of the Y-shaped tube into the patent's nasal passage and terminating about 2 mm from the test site. The step of inserting the first outlet end of a Y-shaped tube into a patent's nasal passage and terminating about 2 mm from the test site may include inserting the first outlet end of the Y-shaped tube into the patent's nasal passage and terminating about 2 mm from the anterior wall of the patient's pyriform sinus. The step of delivering a time and pressure controlled puff of air to an inlet end of the Y-shaped tube may include delivering a plurality of time and pressure controlled puffs of air, each of varying pressure, to the inlet end of the Y-shaped tube.

According to another aspect of the invention, an apparatus for testing sensation in a patient at a test site in the upper aero digestive tract is provided, comprising a flexible fiberoptic telescope with an input port at a first end and an output port at a second end, said input port being in communication with said output port, said flexible fiberoptic telescope being adapted to be inserted at its second end into one of the patient's nasal passage and oral passage, the second end terminating adjacent the test site, a Y-connector with an inlet end and first and second outlet ends, a delivery tube with an inlet end and an outlet end, the outlet end of the delivery tube being attached to the input port of the flexible fiberoptic telescope and the inlet end of the delivery tube being attached to the first outlet end of the Y-connector, a pressure transducer, a sensor tube with an inlet end and an outlet end, the sensor tube inlet end being connected to the second outlet end of the Y-connector and the sensor tube outlet end being connected to the pressure transducer, means for delivering a time and pressure controlled puff of air to the inlet end of the Y-connector, and display means responsive to the pressure transducer for displaying a value of pressure detected by the transducer.

The flexible fiberoptic telescope may further comprise an insertion tube section at its second end detachably connected to a base section at its proximal end, whereby the insertion tube section is inserted into one of the patient's nasal passage and oral passage.

The apparatus may further comprise a flexible sheath for covering at least a part of the flexible fiberoptic telescope. The flexible sheath may be formed as part of the detachable insertion tube section. Further, the distance from the input port of the flexible fiberoptic telescope to the output port of the flexible fiberoptic telescope added to the length of the delivery tube may substantially equal the length of the sensor tube.

According to another aspect of the invention, a method for testing sensation in a patient at a test site in the upper aero digestive tract is provided, comprising connecting a first outlet end of a Y-shaped tube to an input end of an insertion tube section of a flexible fiberoptic telescope, inserting the insertion tube section of the flexible fiberoptic telescope into one of the patient's nasal passage and oral passage so that an output end of the insertion tube section is adjacent the test site, delivering a time and pressure controlled puff of air to an inlet end of the Y-shaped tube, measuring the air pressure at a second outlet end of the Y-shaped tube, and displaying the measured air pressure.

The step of inserting the insertion tube section of the flexible fiberoptic telescope into one of the patient's nasal passage and oral passage so that an output end of the insertion tube section is adjacent the test site may further comprise inserting the insertion tube section into one of the patient's nasal passage and oral passage and terminating the output end of the insertion tube section about 2 mm from the test site.

In addition, the step of inserting the insertion tube section of the flexible fiberoptic telescope into one of the patient's nasal passage and oral passage and terminating the output end of the insertion tube section about 2 mm from the test site may further comprise inserting the insertion tube section into one of the patient's nasal passage and oral passage and terminating the output end of the insertion tube section about 2 mm from the anterior wall of the patient's pyriform sinus.

The step of delivering a time and pressure controlled puff of air to an inlet end of the Y-shaped tube may further comprise delivering a plurality of time and pressure controlled puffs of air, each of varying pressure.

According to another aspect of the present invention an apparatus for testing sensation in a patient at a test site is provided, comprising control means for setting a time duration value and a pressure value of a time and pressure controlled puff of air, means for generating the time and pressure controlled puff of air in response to said set time duration value and said set pressure value, and means, connected to said means for generating, for delivering the controlled puff of air to the test site.

The means for generating a time and pressure controlled puff of air may further comprise a source of high pressure air, a pressure regulator receiving the high pressure air, a valve receiving regulated air from the pressure regulator, and means for controllably driving the valve to open and closed positions.

The means for controllably driving the valve to open and closed positions may further comprise a trigger circuit producing trigger signals, a valve driver producing drive signals responsive to the trigger signals input from the trigger circuit, and an electrically controlled valve, the open or closed state of which is responsive to drive signals input from the valve driver.

The trigger circuit may produce variable duration trigger signals.

According to another aspect of the instant invention an apparatus for testing sensation in a patient at a test site is provided, comprising a Y-shaped tube with an inlet branch having an inlet end and first and second outlet branches having respective first and second outlet ends, the first outlet branch of the Y-shaped tube being inserted into one of the patient's nasal passage and oral passage, the first outlet end terminating adjacent the test site, a pressure transducer connected to the second outlet branch of the Y-shaped tube, axially aligned with the second outlet end, means for delivering a time and pressure controlled puff of air detachably connected to the inlet end of the Y-shaped tube, and display means responsive to the pressure transducer for displaying a value of pressure detected by the transducer.

The first and second outlet branches may be substantially the same length.

The means for delivering a time and pressure controlled puff of air to the inlet end of the Y-shaped tube may further comprise a source of high pressure air, a pressure regulator receiving the high pressure air, a valve, connected between the pressure regulator and the inlet end of the Y-shaped tube, receiving regulated air from the pressure regulator, and means for controllably driving the valve to open and closed positions.

The means for controllably driving the valve to open and closed positions may further comprise a trigger circuit producing trigger signals, a valve driver producing drive signals responsive to the trigger signals input from the trigger circuit, and an electrically controlled valve, the open or closed state of which is responsive to drive signals input from the valve driver.

The trigger circuit may produce variable duration trigger signals.

The display means responsive to the pressure transducer for displaying a value of pressure detected by the transducer may further comprise a transducer circuit responsive to input from the pressure transducer and a display responsive to input from the transducer circuit.

The display may be a Light Emitting Diode display.

According to another aspect of the instant invention an apparatus for testing sensation in a patient at a test site is provided, comprising a Y-connector with an inlet end and first and second outlet ends, a pressure transducer, means for delivering a time and pressure controlled puff of air to the inlet end of the Y-connector, a delivery tube with an inlet end and an outlet end, the delivery tube inlet end being connected to the first outlet end of the Y-connector and the delivery tube outlet end being inserted into the patient's nasal passage and terminating adjacent the test site, a sensor tube with an inlet end and an outlet end, the sensor tube inlet end being connected to the second outlet end of the Y-connector and the sensor tube outlet end being connected to the pressure transducer, and display means responsive to the pressure transducer for displaying a value of pressure detected by the transducer.

The delivery tube and the sensor tube may be substantially the same length.

According to another aspect of the instant invention an apparatus for testing sensation in a patient at a test site is provided, comprising a flexible fiberoptic telescope inserted at its distal end into one of the patient's nasal passage and oral passage, the distal end terminating adjacent the test site, a Y-connector with an inlet end and first and second outlet ends, a delivery tube with an inlet end and an outlet end, the delivery tube being detachably attached to the fiberoptic telescope with the outlet end of the delivery tube adjacent the distal end of the fiberoptic telescope and the inlet end of the delivery tube extending outside the patient and being detachably attached to the first outlet end of the Y-connector, a pressure transducer, a sensor tube with an inlet end and an outlet end, the sensor tube inlet end being connected to the second outlet end of the Y-connector and the sensor tube outlet end being connected to the pressure transducer, means for delivering a time and pressure controlled puff of air to the inlet end of the Y-connector, and display means responsive to the pressure transducer for displaying a value of pressure detected by the transducer.

The delivery tube and the sensor tube may be substantially the same length.

According to another aspect of the instant invention a method for testing sensation in a patient at a test site is provided, comprising generating a time and pressure controlled puff of air, and delivering the controlled puff of air to the test site.

The method may further comprise generating a plurality of time and pressure controlled puffs of air, each succeeding puff of air being of a higher pressure than the last, and delivering the plurality of time and pressure controlled puffs of air to the test site in sequence.

The step of generating a plurality of time and pressure controlled puffs of air may further comprise the step of generating, as a first puff, a puff of air with a subliminal pressure, and as a last puff, a puff of air with a supraliminal pressure.

The method may further comprise generating a plurality of time and pressure controlled puffs of air, each succeeding puff of air being of a lower pressure than the last, and delivering the plurality of time and pressure controlled puffs of air to the test site in sequence.

The step of generating a plurality of time and pressure controlled puffs of air may further comprise the step of generating, as a first puff, a puff of air with a supraliminal pressure, and as a last puff, a puff of air with a subliminal pressure.

According to another aspect of the instant invention a method for testing sensation in a patient at a test site is provided, comprising generating six blocks of time and pressure controlled puffs of air, each block including ten puffs of air, each succeeding puff of air in a block differing by a pressure of about $7.5 \times 10^{-2}$ mm Hg as compared to the preceding puff of air, and delivering each block of time and pressure controlled puffs of air to the test site, with a rest period between blocks of about 30 seconds.

The step of delivering each block of time and pressure controlled puffs of air to the test site may further comprise delivering each puff of air at a random time within a ten second window.

The pressure of the first puff of air in about one-half of the blocks may be subliminal and the last puff of air may be supraliminal, and the pressure of the first puff of air in the other one-half of the blocks may be supraliminal and the pressure of the last puff of air may be subliminal.

According to another aspect of the instant invention a method for testing sensation in a patient at a test site is provided, comprising inserting a first outlet end of a Y-shaped tube into one of the patent's nasal passage and oral passage adjacent the test site, delivering a time and pressure controlled puff of air to an inlet end of the Y-shaped tube, measuring the air pressure at a second outlet end of the Y-shaped tube, and displaying the measured air pressure.

The step of inserting the first outlet end of the Y-shaped tube into a patent's nasal passage adjacent the test site may further comprise inserting the first outlet end of the Y-shaped tube into the patent's nasal passage and terminating about 2 mm from the test site.

The step of delivering a time and pressure controlled puff of air to an inlet end of the Y-shaped tube may further comprise delivering a plurality of time and pressure controlled puffs of air, each of varying pressure, to the inlet end of the Y-shaped tube.

According to another aspect of the instant invention an apparatus for testing sensation in a patient at a test site is provided, comprising a flexible fiberoptic telescope with an input port at a first end and an output port at a second end, said input port being in communication with said output port, said flexible fiberoptic telescope being adapted to be inserted at its second end into one of the patient's nasal passage and oral passage, the second end terminating adjacent the test site, a Y-connector with an inlet end and first and second outlet ends, a delivery tube with an inlet end and an outlet end, the outlet end of the delivery tube being attached to the input port of the flexible fiberoptic telescope and the inlet end of the delivery tube being attached to the first outlet end of the Y-connector, a pressure transducer, a sensor tube with an inlet end and an outlet end, the sensor tube inlet end being connected to the second outlet end of the Y-connector and the sensor tube outlet end being connected to the pressure transducer, means for delivering a time and pressure controlled puff of air to the inlet end of the Y-connector, and display means responsive to the pressure transducer for displaying a value of pressure detected by the transducer.

The flexible fiberoptic telescope may further comprise an insertion tube section at its second end detachably connected to a base section at its proximal end, whereby the insertion tube section is inserted into one of the patient's nasal passage and oral passage.

The apparatus may further comprise a flexible sheath for covering at least a part of the flexible fiberoptic telescope. The flexible sheath may be formed as part of the detachable insertion tube section.

The distance from the input port of the flexible fiberoptic telescope to the output port of the flexible fiberoptic telescope added to the length of the delivery tube may substantially equal the length of the sensor tube.

According to another aspect of the instant invention a method for testing sensation in a patient at a test site is provided, comprising connecting a first outlet end of a Y-shaped tube to an input end of an insertion tube section of a flexible fiberoptic telescope, inserting the insertion tube section of the flexible fiberoptic telescope into one of the patient's nasal passage and oral passage so that an output end of the insertion tube section is adjacent the test site, delivering a time and pressure controlled puff of air to an inlet end of the Y-shaped tube, measuring the air pressure at a second outlet end of the Y-shaped tube, and displaying the measured air pressure.

The step of inserting the insertion tube section of the flexible fiberoptic telescope into one of the patient's nasal passage and oral passage so that an output end of the insertion tube section is adjacent the test site may further comprise inserting the insertion tube section into one of the patient's nasal passage and oral passage and terminating the output end of the insertion tube section about 2 mm from the test site.

The step of delivering a time and pressure controlled puff of air to an inlet end of the Y-shaped tube may further comprise delivering a plurality of time and pressure controlled puffs of air, each of varying pressure.

According to another aspect of the instant invention a method for testing sensation in a patient at a test site is provided, comprising generating a time and pressure controlled puff of air, delivering the controlled puff of air to the test site, and observing when an involuntary reflex occurs in the area of the test site.

The test site may be in the upper aero digestive tract. The test site may be the mucosa overlying the superior laryngeal nerve.

The involuntary reflex may be laryngeal adduction.

The step of observing when the involuntary reflex occurs may comprise viewing said involuntary reflex through a fiberoptic telescope.

The method may further comprise generating a plurality of time and pressure controlled puffs of air, each succeeding puff of air being of a higher pressure than the last, and delivering the plurality of time and pressure controlled puffs of air to the test site in sequence.

The step of generating a plurality of time and pressure controlled puffs of air may further comprise the step of generating, as a first puff, a puff of air with a subliminal pressure, and as a last puff, a puff of air with a supraliminal pressure.

The method may further comprise generating a plurality of time and pressure controlled puffs of air, each succeeding puff of air being of a lower pressure than the last, and delivering the plurality of time and pressure controlled puffs of air to the test site in sequence.

The step of generating a plurality of time and pressure controlled puffs of air may further comprise the step of generating, as a first puff, a puff of air with a supraliminal pressure, and as a last puff, a puff of air with a subliminal pressure.

According to another aspect of the instant invention a method for testing sensation in a patient at a test site is provided, comprising generating six blocks of time and pressure controlled puffs of air, each block including ten puffs of air, each succeeding puff of air in a block differing by a pressure of about 0.2 mm Hg as compared to the preceding puff of air, delivering each block of time and pressure controlled puffs of air to the test site, with a rest period between blocks of about 30 seconds, and observing when an involuntary reflex occurs in the area of the test site.

The test site may be in the upper aero digestive tract. The test site may be the mucosa overlying the superior laryngeal nerve.

The involuntary reflex may be laryngeal adduction.

The step of observing when the involuntary reflex occurs may comprise viewing said involuntary reflex through a fiberoptic telescope.

The step of observing when the involuntary reflex occurs may comprise viewing said involuntary reflex and noting when said involuntary reflex occurs within approximately 1 second after the delivery of each puff of air to the test site.

The pressure of the first puff of air in about one-half of the blocks may be subliminal and the last puff of air may be supraliminal, and the pressure of the first puff of air in the other one-half of the blocks may be supraliminal and the pressure of the last puff of air may be subliminal.

Referring now to the Figs., FIG. 1 shows an upper aero digestive tract sensation measurement apparatus according to a first embodiment of the present invention, which can be used to perform the method according to the present invention. The apparatus is particularly suited for measuring sensation thresholds in the oral cavity, pharynx, and/or larynx. The preferred embodiment will be described with reference to the supraglottic and pharyngeal regions, but this is by way of example and not by way of limitation.

The apparatus comprises a high pressure air supply 1 feeding pressure regulator 3, that regulates the pressure of air delivered to valve 5, which is a normally closed valve. Valve 5 is driven to the open state in response to drive signals from valve driver 7. Valve driver 7 operates in response to trigger signals from trigger circuit 9. In other words, valve driver 7 is responsive to trigger signals from trigger circuit 9 and valve 5 is responsive to drive signals from valve driver 7.

Stimulus output signal port 10 outputs stimulus output signals in response to trigger signals received from trigger circuit 9.

The output of valve 5 is connected to the inlet branch 19a of Y-shaped tube 19. The first outlet branch 19b of Y-shaped tube 19 is inserted into the patient 17 and the second outlet branch 19c of Y-shaped tube 19 is axially aligned with and is terminated by pressure transducer 13. The first outlet branch 19b and the second outlet branch 19c are substantially the same cross-sectional area, shape, and length. Pressure transducer 13 is connected to and provides input to transducer circuit 11, which drives display 15.

The operation of a supraglottic and pharyngeal sensation measurement apparatus according to a first embodiment of the present invention is as follows. The first output branch 19b of Y-shaped tube 19 is inserted into the patient 17 through the patient's nasal passage (not shown). The distal end of the first output branch 19b is inserted deep enough into patent's nasal passage so that it is adjacent a test site (not shown). Pressure regulator 3 is set to a desired pressure value, high pressure air supply 1 is activated and trigger circuit 9 is adjusted to deliver a trigger signal of a desired duration. The trigger signal is delivered from trigger circuit 9 to valve driver 7, which in turn causes valve 5 to enter the open state for the duration of the trigger signal. It should be noted that the Y-shaped tube may be detachable from valve 5 and pressure transducer 13 so that after each use the tube may be disposed of and a new one may be installed in its place.

During the time when valve 5 is driven to the open state, air from pressure regulator 3 is permitted to flow into the input branch 19a of Y-shaped tube 19. The air delivered to the input branch 19a of Y-shaped tube 19 then flows into both the first output branch 19b, where it is delivered to the patient 17, and the second output branch 19c, where it is delivered to pressure transducer 13. Transducer circuit 11 determines the pressure present at pressure transducer 13 and displays such pressure on display 15. Since first outlet branch 19b and second outlet branch 19c are substantially the same cross-sectional area, shape, and length, the pressure displayed on display 15, as representing the pressure at pressure transducer 13, also represents the pressure at the distal end of first outlet branch 19b. Multiple air puffs, of varying durations and pressures, may then be delivered to patient 17 to determine sensory thresholds.

Stimulus output signal port 10 outputs stimulus output signals in response to trigger signals received from trigger circuit 9, whereby the stimulus output signals may serve as a trigger for an oscilloscope (not shown) and/or for physiological recordings on a recorder (not shown). These recordings may include EMG (electromyography) changes in oral cavity, laryngeal, pharyngeal, and esophageal musculature. The stimulus output signal may also be used for synchronizing computer averaging for recording of sensory evoked potentials such as cortical, sub-cortical, and brain-stem evoked responses, as well as other electroencephalographic changes. Such recordings enable non-invasive analysis of both the peripheral nervous system and the brain in conscious and unconscious patients.

Figure 2:
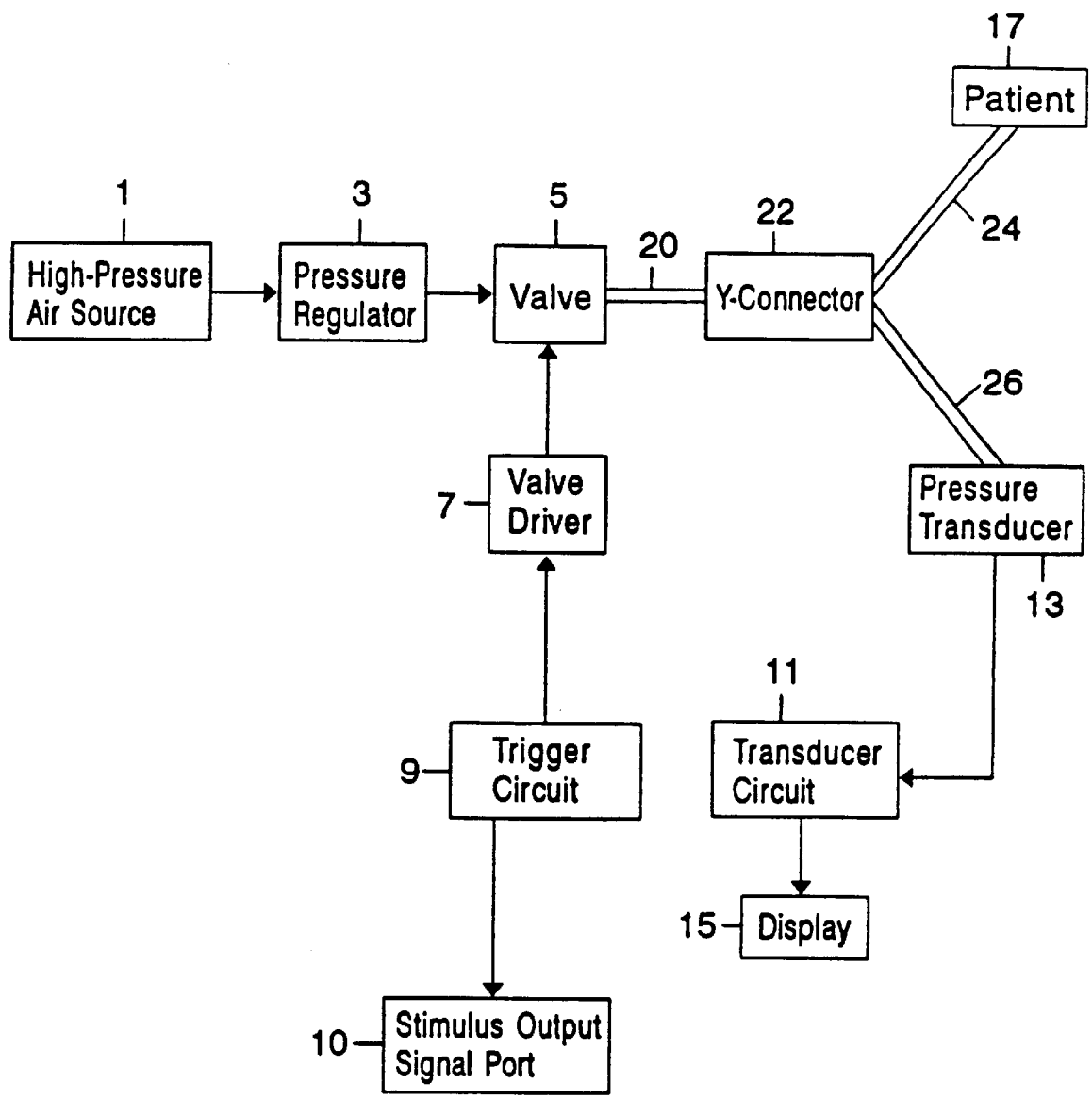
FIG. 2 is an upper aero digestive tract sensation measurement apparatus according to a second embodiment of the present invention.

Referring now to FIG. 2, wherein the same reference numerals of FIG. 1 are applied to the same parts and therefore do not require detailed description, a supraglottic and pharyngeal sensation measurement apparatus according to a second embodiment of the present invention is shown, which can also be used to perform the method according to the present invention. In this Fig., the output of valve 5 is connected to inlet tube 20, which is in turn connected to Y-connector 22 that has two outlet ends. Delivery tube 24 is connected to the first outlet end of Y-connector 22 and sensor tube 26 is connected to the second outlet end of Y-connector 22. Delivery tube 24 and sensor tube 26 are substantially the same length. Delivery tube 24 is inserted into the nasal passage (not shown) of patient 17, with the distal end of delivery tube 24 terminating adjacent the test site (not shown). The distal end of sensor tube 26 is axially aligned with and terminates adjacent to pressure transducer 13. This second embodiment operates in the same manner as the first embodiment.

It should be noted that the delivery tube 24 may be detachable from Y-connector 22 so that after each use the tube may be disposed of and a new one may be installed in its place. Further, inlet tube 20 may likewise be detachable from valve 5 and Y-connector 22 and sensor tube 26 may be detachable from Y-connector 22 and transducer 13.

Figure 3:
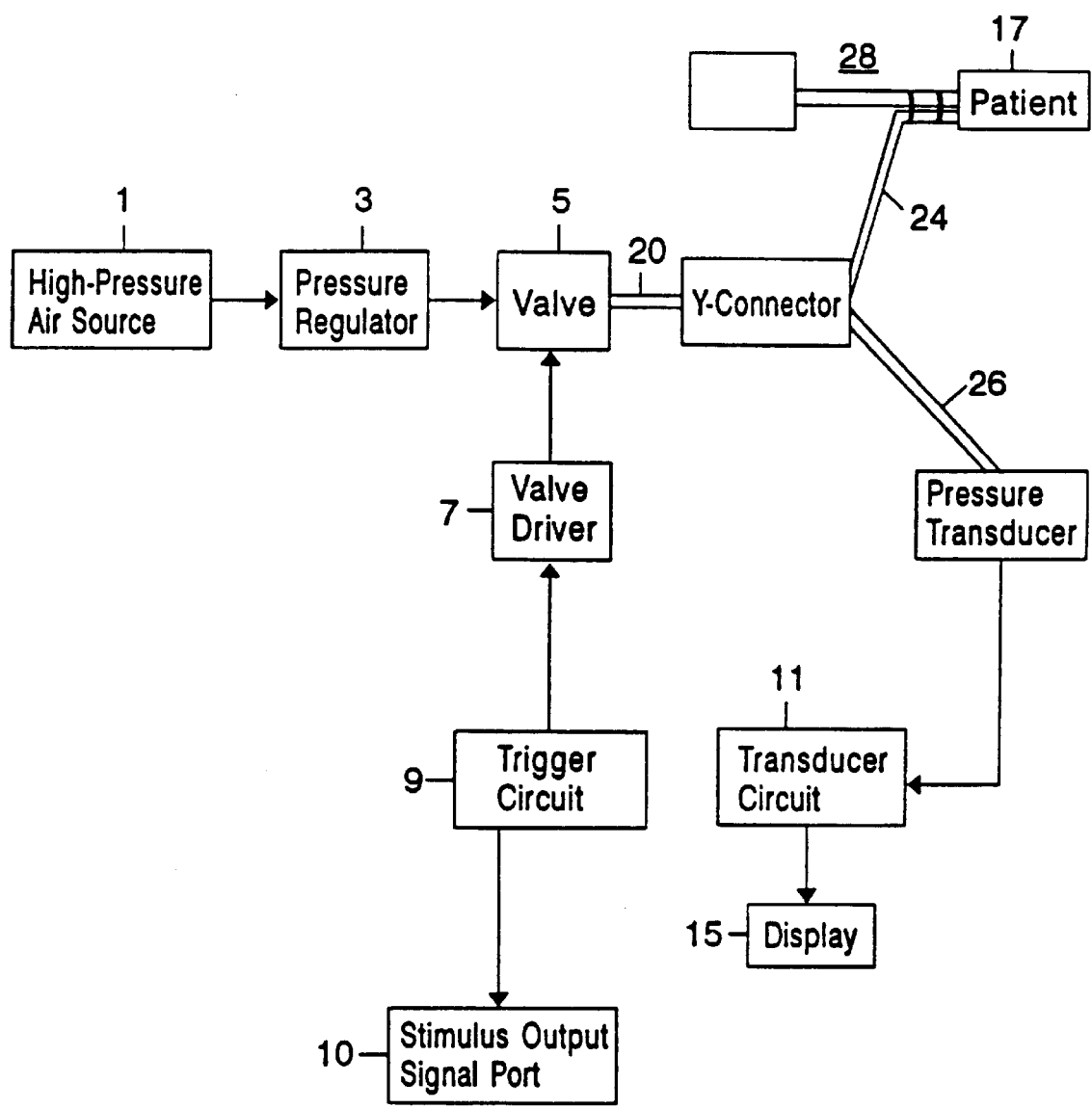
FIG. 3 is an upper aero digestive tract sensation measurement apparatus according to a third embodiment of the present invention.

Referring now to FIG. 3, wherein the same reference numerals of FIG. 1 are applied to the same parts and therefore do not require detailed description, a supraglottic and pharyngeal sensation measurement apparatus according to a third embodiment of the present invention is shown, which can also be used to perform the method according to the present invention. In this Fig., the output of valve 5 is connected to the input tube 20, which is in turn connected to Y-connector 22 that has two outlet ends. Delivery tube 24 is connected to the first outlet end of Y-connector 22 and is attached to the exterior of a flexible fiberoptic telescope 28, with the distal end of delivery tube 24 being adjacent the distal end of flexible fiberoptic telescope 28. In this embodiment, test puffs can be administered to the patent 17 during the course of an otherwise standard laryngoscopic examination. The operation of this third embodiment is the same as that of the first and second embodiments.

It should be noted that in this embodiment the delivery tube 24 may be detachable from Y-connector 22 and flexible fiberoptic telescope 28 so that after each use the tube may be disposed of and a new one may be installed in its place. Further, inlet tube 20 may likewise be detachable from valve 5 and Y-connector 22 and sensor tube 26 may be detachable from Y-connector 22 and transducer 13.

Figure 4:
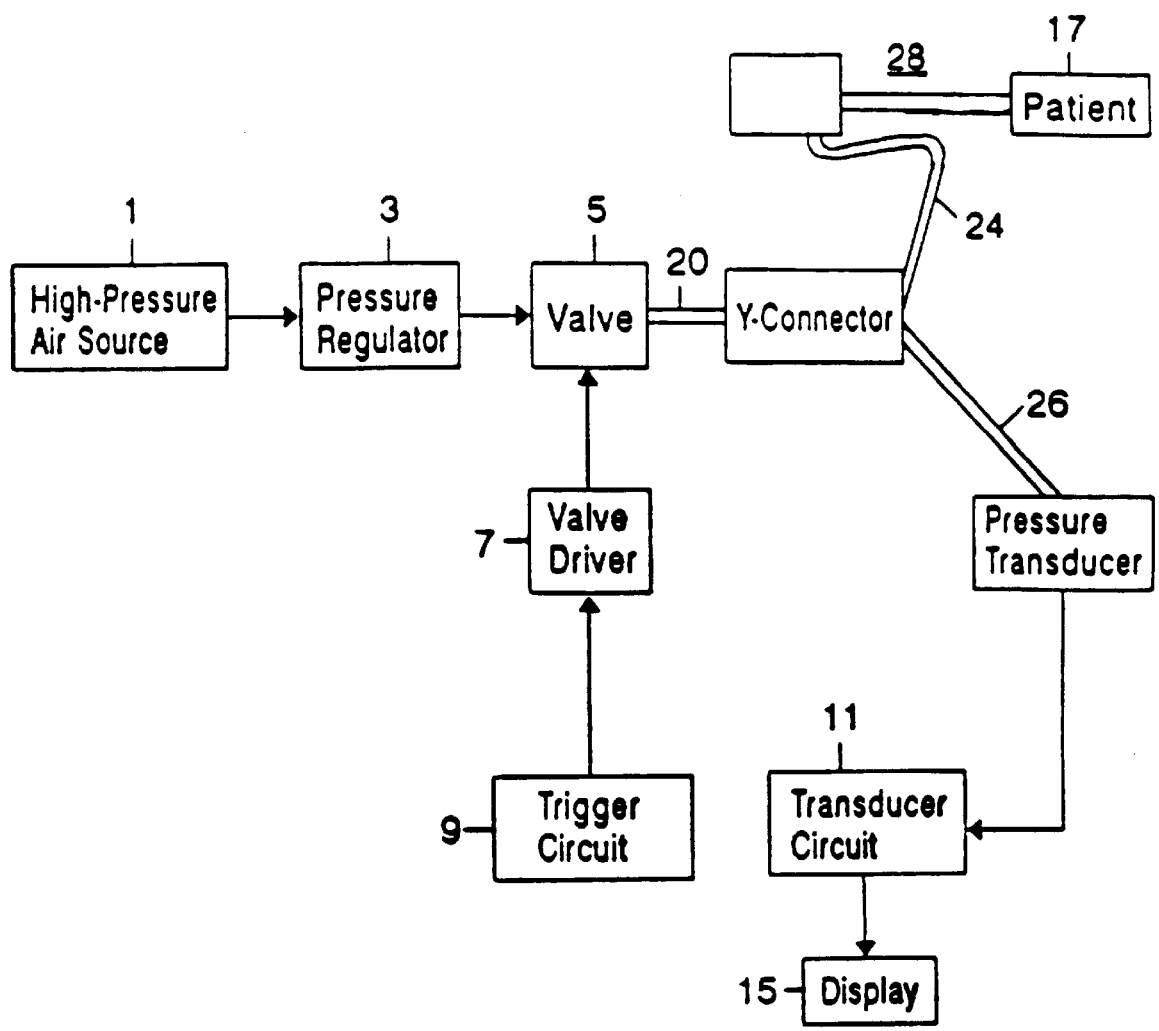
FIG. 4 is an upper aero digestive tract sensation measurement apparatus according to a fourth embodiment of the present invention.
Figure 5:
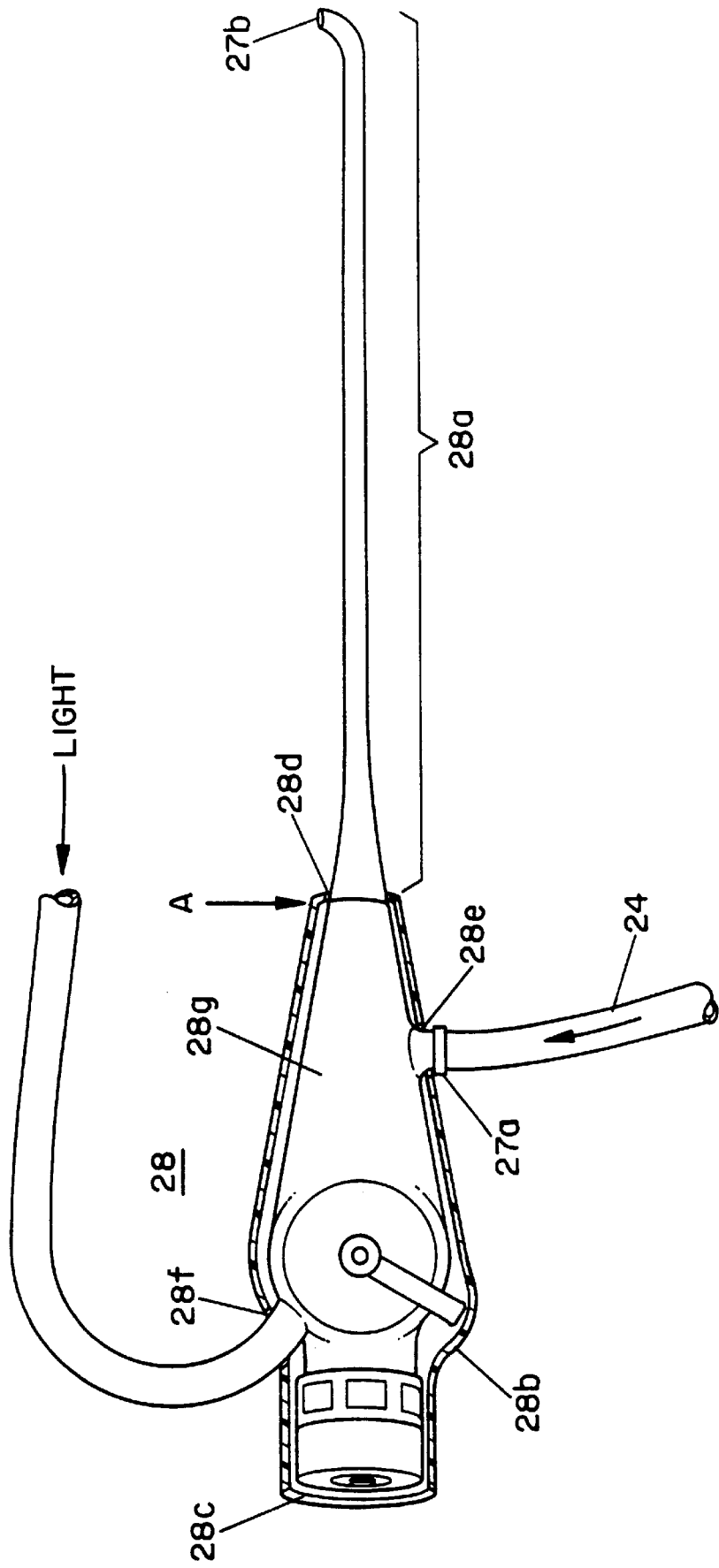
FIG. 5 is a more detailed diagram of the flexible fiberoptic telescope shown in FIG. 4.

Referring now to FIGS. 4 and 5, wherein the same reference numerals of FIG. 3 are applied to the same parts and therefore do not require detailed description, a supraglottic and pharyngeal sensation measurement apparatus according to a fourth embodiment of the present invention is shown, which can also be used to perform the method according to the present invention. In these Figs., the output of valve 5 is connected to the input tube 20, which is in turn connected to Y-connector 22 that has two outlet ends. Delivery tube 24 is connected to the first outlet end of Y-connector 22 and is attached to input port 27a at the proximal end of flexible fiberoptic telescope 28. The input port 27a of the flexible fiberoptic telescope 28 communicates with output port 27b, which is positioned at the distal end of the fiberoptic telescope 28. Thus, the air puffs are received by the flexible fiberoptic telescope 28 at input port 27a and are administered to the patient through output port 27b. In this embodiment, test puffs can be administered to the patent 17 during the course of an otherwise standard laryngoscopic examination. The operation of this fourth embodiment is the same as that of the first, second, and third embodiments. The length of sensor tube 26 should preferably equal the length of the delivery tube 24 plus the length from input port 27a to the output port 27b.

Figure 6:
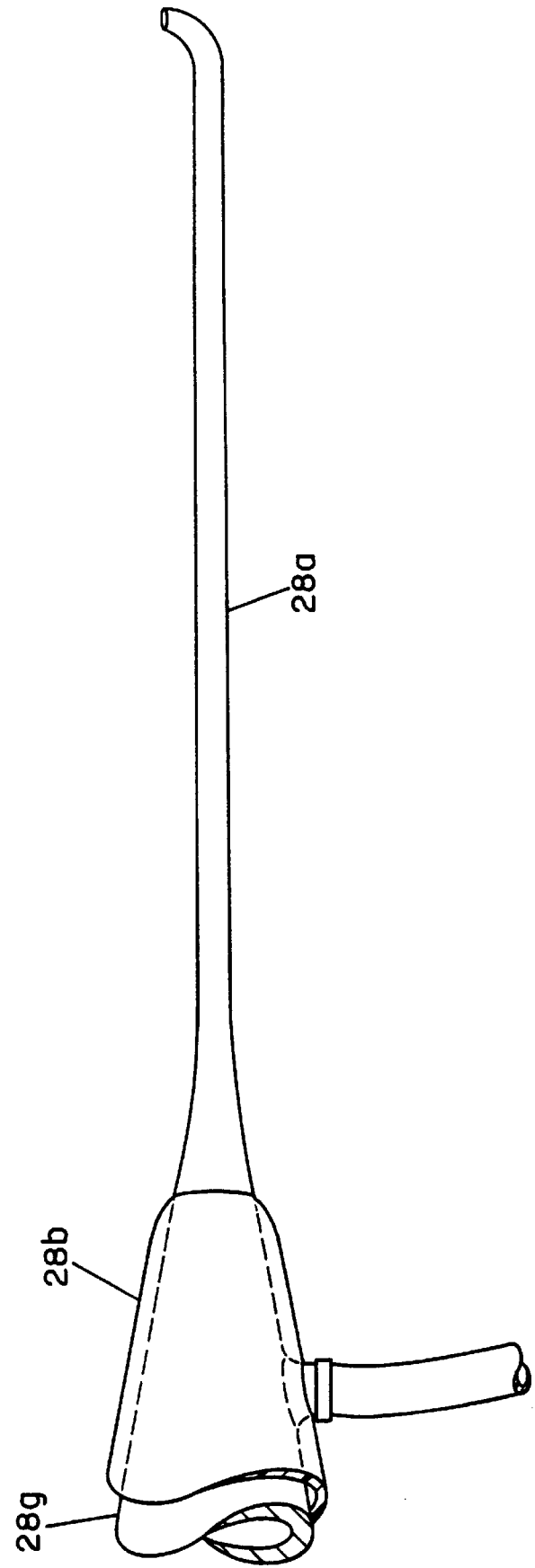
FIG. 6 shows a detachable insertion section and integral sheave which may be used with the apparatus shown in FIG. 5.

In addition, the fiberoptic telescope 28 may have one or more detachable sections 28a, as shown in FIG. 5, for example (this embodiment is shown with one detachable section). This detachable section 28a detaches from base member 28g at point A and is preferably made of an inexpensive material so that it may be disposed of after use and then replaced by a new section. By providing such a detachable, disposable section the instant invention provides a high level of sterility. Further, a skin-tight, disposable sheave 28b may be placed over the base member 28g before use to further increase sterility. The sheave 28b may be open at both ends 28c and 28d and be adapted to form a watertight seal with the flexible fiberoptic telescope 28 at sheave ends 28c and 28d. Of course, such a disposable sheave 28b would be removed and replaced after each use of the apparatus. This sheave 28b may have openings 28e and 28f in register with the various ports of the flexible fiberoptic telescope 28 to allow passage of air at port 28e and fiberoptic cables at port 28f, for example. Such openings would, of course, provide watertight seals between the protected section of the flexible fiberoptic telescope and the patient. In addition, the sheave 28b may be formed as an integral part of detachable section 28a, as shown in FIG. 6. In this case, the sheave 28b would have an open end only at end 28c of FIG. 5.

An experiment conducted using the apparatus and method according to the present invention will now be described.

MATERIALS AND METHODS 20 healthy adults ranging in age from 24–78 with a mean of 44 were studied. There were 12 males and 8 females. To measure supraglottic and pharyngeal sensory level, a pressure and duration controlled puff of air was delivered to the anterior wall of the pyriform sinus (the area innervated by the superior laryngeal nerve) via a secondary port located within a standard flexible fiberoptic telescope (Pentax Precision Instrument Corporation, Orangeburg, N.Y.). The source of pressurized air was a standard air pump for the delivery of aerosolized medications (e.g. SMR Maxi Cabinets, Storz Surgical Specialties, St. Louis, Mo.), but the duration and pressure was controlled and monitored. To determine an individual's sensory pressure threshold, air pressure was varied according to the psychophysical method of limits while the duration of the air puff was held constant at 50 milliseconds (ms). The duration and pressure of the administered air puff was controlled by the electronic circuitry, pressure gauge and pressure transducer of the instant invention.

To deliver a precise amount of air pressure to the test site in the pharynx and larynx, small diameter flexible tubing was attached to the fiberoptic telescope and was matched by a substantially identical length of tubing travelling via a Y-connector to the pressure transducer (Motorola, Inc. Phoenix, Ariz.) so that substantially the same pressure being delivered to the patient was simultaneously being delivered to the pressure transducer. The flexible fiberoptic telescope was passed into the patient via the nasal passage and the distal tip was advanced until it was located 2 mm from the test site. The distal tip of the second air tube branch was fixed 2 mm from the pressure transducer.

PROCEDURE

The fiberoptic telescope was inserted into the nasal passage and the patient was given a 1 minute rest period to adapt to the laryngoscope and prepare for testing. The testing procedure began by orienting the subject to the stimulus with a suprathreshold stimulus given for five seconds, a duration 100 times as long as that of the test air puff. After a 15 second rest period, six blocks of stimulus administration trials were given. Each trial lasted for approximately 10 seconds, with a 10 second intertrial rest interval. The air puff was administered after a verbal announcement of the beginning of the trial at a random time from 2 to 8 seconds within the ten second trial interval. A detection response was deemed to occur when the subject raised their hand within 2 seconds of actual stimulus presentation. Three blocks of descending pressure stimulus presentations and three blocks of ascending pressure stimulus presentation were randomly ordered for each subject. Within a block, air puffs were presented in sequential steps of 10 test unit changes (each unit is equivalent to $7.5 \times 10^{-2}$ mm Hg). The sequential steps ran from subliminal to supraliminal for ascending blocks and from supraliminal to subliminal for descending blocks. A 30 second rest period separated the blocks. The mean of the lowest detected pressures from the six blocks was used as that subject's sensory threshold. Both the right and left sides of the pharynx and supraglottic larynx were studied. Each week the air pump was calibrated by a pressure gauge that was attached to the pump.

All testing was performed over a one year period and each subject was tested at least twice over this time period. In addition, three subjects were tested four times over a three month period.

STATISTICAL ANALYSIS

To determine differences between right and left sides the Student's T-test was used. To determine age related changes in pharyngeal and supraglottic sensation, a one way analysis of variance was used. To determine reliability of this device and method, intraclass correlation analysis was performed.

RESULTS 204 trials were conducted in 20 healthy adults ranging in age from 24–78 with a mean of 44. The age breakdown of subjects by decade is located in the Table 1. The results were as follows: Overall, supraglottic and pharyngeal sensory pressure thresholds were 2.09 mm Hg (+/−0.15). Testing for normality revealed a normal distribution of data points. Using the Students T-test, there was no statistically significant difference between the right and left sides. Intraclass correlation revealed excellent consistency (^R=0.80).

Seven of the twenty subjects studied were over 60 years of age. There appeared to be age-related changes in supraglottic and pharyngeal sensory discrimination thresholds which were statistically significant. Specifically, patients over 60 had a sensory discrimination threshold of 2.34 mm Hg (+/−0.07) while patients less than 60 had a sensory discrimination threshold of 2.06 mm Hg (+/−0.11), p<0.0001 (Table 1).

At suprathreshold sensory pressure levels, air puff stimulation generally resulted in gagging by the test subject. Repeat sensory testing after the gagging ceased did not alter sensory pressure thresholds. The duration of testing was on the average no more than 10 minutes longer than the time it took to perform a typical flexible fiberoptic laryngoscopic examination.

In more than 200 trials there were absolutely no adverse reactions to the sensory testing procedure. In particular, there were no episodes of epistaxis, infection or airway compromise.

DISCUSSION

The need for objectively evaluating supraglottic and pharyngeal sensation has already been elaborated. Utilizing the basic principles of air puff stimulation a new apparatus and method has been described. In 204 trials in 20 subjects, our new method has been found to be easily and reproducibly performed, safe and a statistically accurate method of testing.

An interesting finding was that there was a statistically significant difference between sensory thresholds of person younger and older than 60 years. Studies on aging and sensation have established that as one ages sensory discriminatory ability diminished in the oral cavity (10, 11). In general, as one gets older aspiration during swallowing is more likely to occur (2, 12). The primary explanations for these observations are oral and pharyngeal motor dysfunctions such as abnormal lingual activity, poor lingual-palatal seal and pharyngeal pooling. The possible contribution of pharyngeal and supraglottic sensory abnormalities towards the development of aspiration has not been addressed.

It is our hypothesis that as one gets older, supraglottic and pharyngeal sensory discrimination thresholds become progressively greater. This sensory deficit may compound the known motor deficits thus playing a significant role in the development of dysphagia and/or aspiration in these patients.

In the embodiments of the instant invention discussed above, air pulse stimuli are delivered to the mucosa overlying the superior laryngeal nerve. The tests described were psychophysical tests which required a certain amount of cognitive ability by the test subject. In this other embodiment, one's cognitive ability is not important, as now an involuntary reflex—laryngeal adduction or vocal-cord closure—is attempted to be elicited by a pulse of air. A suprathreshold air pulse to the mucosa overlying the superior laryngeal nerve will result in marked transient laryngeal adduction. In this embodiment, the sensory discrimination threshold is not where the test subject indicates that an air pulse is felt; rather, the sensory discrimination threshold in this embodiment is the point (in millimeters of mercury pressure) where the test subject's vocal cords close in response to an air-pulse stimulus.

In other words, one does not have to elicit a voluntary response from the patient; one solely has to stimulate the target site with just enough air pressure to elicit this involuntary reflex of transient, marked vocal-cord adduction. This embodiment of laryngopharyngeal sensory discrimination testing will be useful as a means of assessing motor and sensory reflexes in various locations, most notably in the upper aero digestive tract.

This embodiment of the present invention solves the problem of performing a psychophysical test in a cognitively impaired individual. One can now perform laryngopharyngeal sensory discrimination testing on a patient whose cognitive abilities are impaired.

By way of background relating to this embodiment, it is noted that traditionally, in order to measure the swallowing reflex and the vocal-cord closing reflex, the thinking had been to stimulate the tissues in the back of the oral cavity; in particular, the palatal and pharyngeal mucosa. Stimulation of this area would result in what is commonly known as the gag reflex. The gag reflex sensory arm is effected by the ninth cranial nerve. However, it is advantageous not to stimulate the ninth cranial nerve but, rather, the cranial nerve we are interested in stimulating is the superior laryngeal branch of the tenth cranial nerve. Therefore, the gag reflex is a poor approximation of the swallowing and laryngeal closure reflexes.

There currently exists no other way to noninvasively monitor the laryngeal closure reflex other than by discrete air-pulse stimulation of the tissues in the hypopharynx and larynx.

By using discrete air-pulse stimulation of the tissues in the hypopharynx and larynx one can now not only assess sensory discrimination in this region in a patient whose cognitive abilities are impaired, but also can monitor the entire motor and sensory aspects of this reflex arc. This would have widespread use not only in patients who are at risk for aspiration and pneumonia, but whose cognitive abilities may be impaired. The groups of patients that may benefit from this embodiment of the instant invention include the following: (1) stroke patients whose cognitive abilities are affected because of the stroke itself; (2) elderly patients who are suffering from various forms of senile dementia; (3) people with Alzheimer's disease.

Because this embodiment of the instant invention is not a psychophysical test, the previous protocol relating to the psychophysical testing parameters will not be necessary. Simply, an air puff 50 milliseconds in duration and varying in intensity from zero millimeters of mercury to ten millimeters of mercury may be delivered by an internal port located within a standard flexible fiber-optic telescope. The nose may be anesthetized with 1% Xylocaine w/epinephrine 1/1,000,000 that is placed on a cotton tip applicator and passed along the floor of the nose for a distance of about 1 cm. from the nasal vestibule. No other anesthesia need be given. The applicator is removed and a flexible fiber-optic telescope is inserted into the nasal passage. The distal tip of the scope may be advanced, under direct vision, until it is located about 2.0 mm from the test site. The patient may then be given a one-minute rest period to adapt to the fiber optic telescope and to prepare for testing. To determine an individual's sensory and motor reflex pressure threshold air pressure may be varied while the duration of the air puff may be held constant at 50 about milliseconds.

In order to determine the motor and sensory laryngeal reflex threshold, six blocks of stimulus trials may be given, each trial lasting for approximately ten seconds with a ten-second interatrial interval. Once the air puff is administered what is looked for is brief vocal-cord closing within about one second of stimulus delivery. Three blocks of descending pressure stimulus presentations and three blocks of ascending pressure-stimulus presentations may be randomly ordered for each test subject. Within a block, air puffs may be presented within sequential steps of about 0.2 millimeters of mercury; from subliminal to supraliminal for ascending blocks; and from supraliminal to subliminal for descending blocks. A thirty-second rest period may separate the blocks. The mean of the lowest detected pressures from the six blocks which elicited brief laryngeal closure may be used as that subject sensory and motor reflex threshold.

In this way, what the examiner is looking for is not the patient's voluntary response, but the elicitation of the involuntary reflex vocal cord closure.

This embodiment of the instant invention will enable one to include many more test subjects as the motor branch of the vocal cord reflex is being examined in addition to the sensory branch without requiring voluntary patient cognitive responses.

It must be noted that although the present invention is described by reference to particular embodiments thereof, many changes and modifications of the invention may become apparent to those skilled in the art without departing from the spirit and scope of the invention, which is only limited by the appended claims. For example, the first outlet branch of the Y-shaped tube or the delivery tube could be integrated into a flexible fiberoptic telescope instead of being attached thereto. Additionally, the first and second outlet branches of the Y-shaped tube could be of different lengths or cross-sections, with the transducer circuit being calibrated accordingly, so that the display nevertheless displays the pressure at the distal end of the first outlet branch. Likewise, the delivery tube and the sensor tube could be of different lengths or cross-sections, with a similar calibration correction made by the transducer circuit. Therefore, the embodiments shown and described are only illustrative, not restrictive.

TABLE 1

SUPRAGLOTTIC SENSORY DISCRIMINATION THRESHOLDS (mm Hg)

| AGE | N | MEAN +/– S.D. | |
|---|---|---|---|
| 20–30 | 5 | 2.03 +/– 0.14 | |
| 31–40 | 7 | 2.06 +/– 0.10 | 2.06 +/– 0.11* |
| 41–50 | 1 | 2.10 +/– 0.80 | |
| 51–60 | 0 | | |
| 61–70 | 2 | 2.25 +/– 0.08 | 2.34 +/– 0.07 |
| 71–80 | 5 | 2.40 +/– 0.04 | |
| TOTAL | 20 | 2.09 +/– 0.15 | |

*$p < .0001$

REFERENCES

1. Dellon, A. L.: Evaluation of Sensibility and Re-Education of The Sensation in The Hand, John D. Lucas Printing Co., Baltimore, Md. 1988, pp. 95–113.
2. Feinberg, M. J., Ekberg, O.: Videofluoroscopy in Elderly Patients With Aspiration: Importance of Evaluating Both Oral and Pharyngeal Stages of Deglutition. AJR 156: 293–296, 1991.
3. Gresham, S. L.: Clinical Assessment and Management of Swallowing Difficulties After Stroke. Med J Australia. 153: 397–399, 1990.
4. Flores, T. C., Wood, B. G., Levin H. L., Koegal, L., Tucker, H. M.: Factors in Successful Deglutition Following Supraglottic Laryngeal Surgery. Ann Otol Rhinol Laryngol. 91: 579–583, 1982.
5. Ogura, J. H.: Hyoid Muscle Flap Reconstruction in Subtotal Supraglottic Laryngectomy as a More Rapid Rehabilitation of Deglutition: 14 cases. Laryngoscope. 89: 1522–1524, 1979.
6. Durham, D. G., Bigliano, R. P., Masino, J. A.: Pneumatic Applanation Tonometer. Trans Am Acad Ophth Otolaryngol. 69: 1029–1047, 1965.
7. Talbot, W. H., Darian-Smith, I., Kornhuber, H. H., Mountcastle, V. B.: The Sense of Flutter Vibration: Comparisons of Human Capacity with Responses Patterns of Mechanoreceptive Afferents from the Monkey Hand. J Neurol Physiol. 31: 301–334, 1968.
8. Gardner, E. P., Spencer, W. A.: Sensory Funneling. I. Psychophysical Observations of Human Subjects and Responses of Cutaneous Mechanoreceptive Afferents in the Cat to Patterned Skin Stimuli. J Neuro Physiol. 35: 954–977, 1972.
9. Alskin, S. E., Spencer, W. A.: Cutaneous Masking. I. Psychophysical Observations on Interactions of Multipoint Stimuli in Man. J Neurol Physiol. 42: 1048–1060, 1979.
10. Calhoun, K. H., Gibson, B., Hartley, L., Minton, J., Hokanson, J. A.: Age-Related Changes in Oral Sensation. Laryngoscope. 102: 109–116, 1992.
11. Aviv, J. E., Hecht, C., Weinberg, H., Dalton, J. F., Urken, M. L.: Surface Sensibility of the Floor of Mouth and Tongue in Healthy Controls and Radiated Patients. Otolaryngol Head Neck Surg. 107: 418–423, 1992.
12. Kilmann, W., Goyal, R.: Disorders of Pharyngeal and Upper Esophageal Sphincter Motor Function. Arch Int Med. 136: 529–601, 1976.

What is claimed is:

1. An apparatus for testing sensation in a patient at a test site in the upper aero digestive tract, comprising:
   a flexible fiberoptic telescope with an input port at a first end and an output port at a second end, said input port being in communication with said output port;

said flexible fiberoptic telescope being adapted to be inserted at its second end into one of the patient's nasal passage and oral passage, the second end terminating adjacent the test site;

a Y-connector with an inlet end and first and second outlet ends;

a delivery tube with an inlet end and an outlet end, the outlet end of the delivery tube being attached to the input port of the flexible fiberoptic telescope and the inlet end of the delivery tube being attached to the first outlet end of the Y-connector;

a pressure transducer;

a sensor tube with an inlet end and an outlet end, the sensor tube inlet end being connected to the second outlet end of the Y-connector and the sensor tube outlet end being connected to the pressure transducer;

means for delivering a time and pressure controlled puff of air to the inlet end of the Y-connector; and display means responsive to the pressure transducer for displaying a value of pressure detected by the transducer.

2. The apparatus of claim 1, wherein the flexible fiberoptic telescope further comprises an insertion tube section at its second end detachably connected to a base section at its proximal end, whereby the insertion tube section is inserted into one of the patient's nasal passage and oral passage.

3. The apparatus of claim 2, further comprising a flexible sheath for covering at least a part of the flexible fiberoptic telescope.

4. The apparatus of claim 3, wherein the flexible sheath is formed as part of the detachable insertion tube section.

5. The apparatus of claim 4, wherein the distance from the input port of the flexible fiberoptic telescope to the output port of the flexible fiberoptic telescope added to the length of the delivery tube substantially equals the length of the sensor tube.

6. A method for testing sensation in a patient at a test site, comprising:

generating a time and pressure controlled puff of air;

delivering the controlled puff of air to the test site; and observing when an involuntary reflex occurs in the area of the test site.

7. The method for testing sensation of claim 6, wherein said test site is in the upper aero digestive tract.

8. The method for testing sensation of claim 7, wherein said test site is the mucosa overlying the superior laryngeal nerve.

9. The method for testing sensation of claim 8, wherein said involuntary reflex is laryngeal adduction.

10. The method for testing sensation of claim 6, wherein said step of observing when the involuntary reflex occurs comprises viewing said involuntary reflex through a fiberoptic telescope.

11. The method for testing sensation in a patient at a test site of claim 6, further comprising:

generating a plurality of time and pressure controlled puffs of air, each succeeding puff of air being of a higher pressure than the last; and delivering the plurality of time and pressure controlled puffs of air to the test site in sequence.

12. The method for testing sensation in a patient at a test site of claim 11, wherein the step of generating a plurality of time and pressure controlled puffs of air further comprises the step of generating, as a first puff, a puff of air with a subliminal pressure, and as a last puff, a puff of air with a supraliminal pressure.

13. The method for testing sensation in a patient at a test site of claim 6, further comprising:

generating a plurality of time and pressure controlled puffs of air, each succeeding puff of air being of a lower pressure than the last; and delivering the plurality of time and pressure controlled puffs of air to the test site in sequence.

14. The method for testing sensation in a patient at a test site of claim 13, wherein the step of generating a plurality of time and pressure controlled puffs of air further comprises the step of generating, as a first puff, a puff of air with a supraliminal pressure, and as a last puff, a puff of air with a subliminal pressure.

15. A method for testing sensation in a patient at a test site, comprising:

generating six blocks of time and pressure controlled puffs of air, each block including ten puffs of air, each succeeding puff of air in a block differing by a pressure of about 0.2 mm Hg as compared to the preceding puff of air;

delivering each block of time and pressure controlled puffs of air to the test site, with a rest period between blocks of about 30 seconds; and observing when an involuntary reflex occurs in the area of the test site.

16. The method for testing sensation of claim 15, wherein said test site is in the upper aero digestive tract.

17. The method for testing sensation of claim 16, wherein said test site is the mucosa overlying the superior laryngeal nerve.

18. The method for testing sensation of claim 17, wherein said involuntary reflex is laryngeal adduction.

19. The method for testing sensation of claim 15, wherein said step of observing when the involuntary reflex occurs comprises viewing said involuntary reflex through a fiberoptic telescope.

20. The method for testing sensation of claim 15, wherein said step of observing when the involuntary reflex occurs comprises viewing said involuntary reflex and noting when said involuntary reflex occurs within approximately 1 second after the delivery of each puff of air to the test site.

21. The method for testing sensation of claim 15, wherein the pressure of the first puff of air in about one-half of the blocks is subliminal and the last puff of air is supraliminal, and the pressure of the first puff of air in the other one-half of the blocks is supraliminal and the pressure of the last puff of air is subliminal.

* * * * *